US012685827B2

(12) United States Patent
Miley et al.

(10) Patent No.: US 12,685,827 B2
(45) Date of Patent: Jul. 21, 2026

(54) AUTOINJECTOR SUB-ASSEMBLY

(71) Applicant: SHL MEDICAL AG, Zug (CH)

(72) Inventors: Thad Miley, Boca Raton, FL (US);
Brian Maxfield, Delray Beach, FL
(US); Randall Goldfarb, Boca Raton,
FL (US)

(73) Assignee: SHL Medical AG, Zug (CH)

( * ) Notice: Subject to any disclaimer, the term of this
patent is extended or adjusted under 35
U.S.C. 154(b) by 605 days.

(21) Appl. No.: 18/029,197

(22) PCT Filed: Oct. 29, 2021

(86) PCT No.: PCT/EP2021/080126
§ 371 (c)(1),
(2) Date: Mar. 29, 2023

(87) PCT Pub. No.: WO2022/101031
PCT Pub. Date: May 19, 2022

(65) Prior Publication Data
US 2023/0364351 A1      Nov. 16, 2023

Related U.S. Application Data

(60) Provisional application No. 63/114,209, filed on Nov.
16, 2020.

(30) Foreign Application Priority Data

Dec. 15, 2020      (EP) ...................................... 20214325

(51) Int. Cl.
*A61M 5/32*      (2006.01)
(52) U.S. Cl.
CPC ................................. *A61M 5/3204* (2013.01)

(58) Field of Classification Search
CPC .......................... A61M 5/3204; A61M 5/3213
See application file for complete search history.

(56) References Cited

U.S. PATENT DOCUMENTS

| | | | |
|---|---|---|---|
| 9,028,451 B2 | 5/2015 | Jennings | |
| 10,207,059 B2 | 2/2019 | Perche et al. | |

(Continued)

FOREIGN PATENT DOCUMENTS

| | | |
|---|---|---|
| EP | 2021057 B1 | 8/2010 |
| EP | 3302642 B1 | 9/2019 |

(Continued)

OTHER PUBLICATIONS

International Search Report and Written Opinion for Int. App. No.
PCT/EP2021/080126, mailed Feb. 3, 2022.

*Primary Examiner* — William R Carpenter
(74) *Attorney, Agent, or Firm* — McDonnell Boehnen
Hulbert & Berghoff LLP

(57)      ABSTRACT

The present disclosure concerns an autoinjector sub-assem-
bly having a cap with a tubular housing extending from a
proximal closed end to a distal open end and an arm attached
to the tubular housing, wherein the arm extends in the axial
direction from the distal open end, a syringe holder having
a tubular body with a tubular flange attached to the proximal
end of the tubular body, the tubular flange having an inner
surface facing towards the axis, wherein the arm of the cap
is between the axis and the inner surface of the flange of the
syringe holder, wherein the arm of the cap has a protrusion
extending in the radial direction away from the axis, and
wherein the arm of the cap has a protrusion extending in the
radial direction towards the axis.

14 Claims, 4 Drawing Sheets

(56)          References Cited

U.S. PATENT DOCUMENTS

| | | | |
|---|---|---|---|
| 2016/0243315 A1* | 8/2016 | Perche ................ | A61M 5/3204 |
| 2017/0258998 A1 | 9/2017 | Stamp | |
| 2018/0140782 A1 | 5/2018 | Kemp et al. | |
| 2018/0311443 A1* | 11/2018 | Maxfield ............. | A61M 5/3204 |
| 2019/0117902 A1 | 4/2019 | Hodgson | |
| 2019/0374727 A1 | 12/2019 | Dugand et al. | |

FOREIGN PATENT DOCUMENTS

| | | | |
|---|---|---|---|
| EP | 1998831 B1 | 10/2020 | |
| WO | 2010/136076 A1 | 12/2010 | |
| WO | 2010/136078 A1 | 12/2010 | |
| WO | 2014/009705 A1 | 1/2014 | |
| WO | 2015/044561 A1 | 4/2015 | |

* cited by examiner

AUTOINJECTOR SUB-ASSEMBLY

CROSS REFERENCE TO RELATED APPLICATIONS

The present application is a U.S. National Phase application pursuant to 35 U.S.C. § 371 of International Application No. PCT/EP2021/080126 filed Oct. 29, 2023, which claims priority to U.S. Provisional Patent Application No. 63/114,209 filed Nov. 16, 2020 and European Patent Application No. 20214325.1, filed Dec. 15, 2020. The entire disclosure contents of these applications are herewith incorporated by reference into the present application.

TECHNICAL FIELD

The present disclosure concerns autoinjector sub-assemblies, and particularly autoinjector sub-assemblies comprising a cap and a syringe holder.

BACKGROUND

Autoinjectors often include a cap made of several different pieces, for example plastic portions along with a rigid needle shield remover arranged inside the cap to grip and remove a rigid needle shield when removing the cap. A particular difficulty in design in this area of an autoinjector is that there is very little space and components tend to be small and flimsy. Nevertheless, it has been appreciated that current designs can be improved by implementation of the present disclosure outlined below.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

In a first aspect, the present disclosure concerns an autoinjector sub-assembly extending along an axis in an axial direction from a proximal end to a distal end, the autoinjector-sub-assembly comprising a cap comprising a tubular housing extending from a proximal closed end to a distal open end and an arm attached to the tubular housing, wherein the arm extends in the axial direction from the distal open end, a syringe holder comprising a tubular body extending from a proximal end to a distal end and a tubular flange attached to the proximal end of the tubular body, the tubular flange comprising an inner surface facing towards the axis, wherein the arm of the cap is between the axis and the inner surface of the flange of the syringe holder, wherein the arm of the cap comprises a protrusion extending in the radial direction away from the axis (this can engage the inner surface of the flange when the cap is removed), and wherein the arm of the cap comprises a protrusion extending in the radial direction towards the axis (this can engage a distally-facing surface of a medicament delivery member shield of a syringe).

This autoinjector sub-assembly, when incorporated in an autoinjector, can enable the removal of a medicament delivery member shield (for example a rigid needle medicament delivery member shield, particularly a rigid needle shield) from a syringe. In particular, the protrusion extending in the radial direction towards the axis can engage a distally-facing surface of a medicament delivery member shield of a syringe, resulting in the needle shield being removed from a syringe when the cap is removed from the autoinjector. This approach can reduce the number of components compared to existing solutions using multi-component caps, and it can also reduce the number of materials used in the cap, as the entire cap can be made of a single material. The arms of the cap can be supported by the flange of the syringe holder, thereby helping to keep the arms in place gripping the medicament delivery member shield.

Preferably, the inner surface of the flange is further from the axis at the distal end of the inner surface than at the proximal end of the inner surface. Preferably, the flange of the syringe holder extends fully around the axis in a circumferential direction relative to the axis. This can help with removal of a medicament delivery member shield such as a needle shield during cap removal. Preferably, the distance of the inner surface from the axis continually reduces when travelling along the flange from the distal end of the inner surface to the proximal end of the inner surface. This can help with removal of a medicament delivery member shield during cap removal. This can also help with assembly.

Preferably, the syringe holder comprises a flexible arm extending in the axial direction from a proximal end to a distal end, wherein the distal end of the arm is attached to the body and the proximal end of the arm is movable in the radial direction relative to the body. This can help support a syringe.

Preferably, the cap is a single integral part. Preferably, the autoinjector sub-assembly comprises a syringe, the syringe comprising a medicament container, a medicament delivery member shield, and a medicament delivery member attached to the medicament container, wherein the medicament delivery member is inside the medicament delivery member shield.

The autoinjector sub-assembly may be characterised in that a proximally-facing surface of the protrusion extending in the radial direction towards the axis abuts a distally facing surface of the medicament delivery member shield.

The autoinjector sub-assembly may be characterised in that, a proximally-facing surface of the protrusion extending in the radial direction towards the axis is spaced apart in the axial direction from a distally facing surface of the medicament delivery member shield. This can reduce the initial force required to start removing the cap. This can also allow a medicament delivery member shield to pass (during assembly) the protrusion extending in the radial direction towards the axis (due to the protrusion moving away from the axis in the radial direction), whilst still allowing the flange to support the protrusion extending in the radial direction towards the axis during removal of the cap to ensure that the protrusion extending in the radial direction towards the axis engages the distally facing surface of the medicament delivery member shield to remove the medicament delivery member shield along with the cap during removal of the cap.

Preferably, the autoinjector sub-assembly comprises a housing, wherein the syringe holder is attached to the housing.

Preferably, the protrusion extending in the radial direction away from the axis is configured to engage the inner surface of the flange when the cap is removed from an autoinjector comprising the autoinjector sub-assembly. Preferably, the protrusion extending in the radial direction towards the axis is configured to engage a distally-facing surface of a medicament delivery member shield of a syringe when the cap is removed from an autoinjector comprising the autoinjector sub-assembly.

Preferably, the tubular body of the syringe holder comprises a recess or cut-out, wherein the recess or cut-out is aligned in a radial direction relative to the axis with the protrusion extending in the radial direction away from the axis. This can allow the protrusion extending in the radial direction away from the axis to move away from the axis during assembly, although the recess/cut-out is not required for this, as this space for movement during assembly can be provided in other ways—such as by extending the sloped inner surface of the flange further in the distal direction compared to the example in FIG. 5, and by providing a gap between the sloped inner surface of the flange and the protrusion extending in the radial direction away from the axis.

A second aspect of the present disclosure concerns an autoinjector comprising an autoinjector sub-assembly as described above.

A third aspect of the present disclosure concerns a cap comprising a body, the body extending from a closed proximal end to an open distal end, the cap comprising an arm attached to the distal end of the tubular body, wherein the arm comprises a protrusion extending in the radial direction away from the axis to engage a flange on a syringe holder when the cap is removed during use of a medicament delivery device comprising the cap, wherein the arm comprises a protrusion extending in the radial direction towards the axis to engage the distal end of a medicament delivery member shield of a syringe when the cap is removed during use of a medicament delivery device comprising the cap. Preferably, the cap is a single integral part.

A fourth aspect of the present disclosure concerns a syringe holder comprising a body extending from a proximal end to a distal end and a flange attached to the proximal end of the body, the flange comprising an inner surface facing towards the axis, wherein the flange is configured to engage a protrusion on an arm on a cap when said cap is removed during use of a medicament delivery device comprising the syringe holder. Preferably, the flange is angled in the axial direction so that a proximal end of the inner surface of the flange is closer to a central axis of the syringe holder than a distal end of the inner surface of the flange.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

BRIEF DESCRIPTION OF THE DRAWINGS

Embodiments of the present disclosure will now be described by way of example only and with reference to the accompanying drawings, in which.

DETAILED DESCRIPTION

Figures 1, 2:
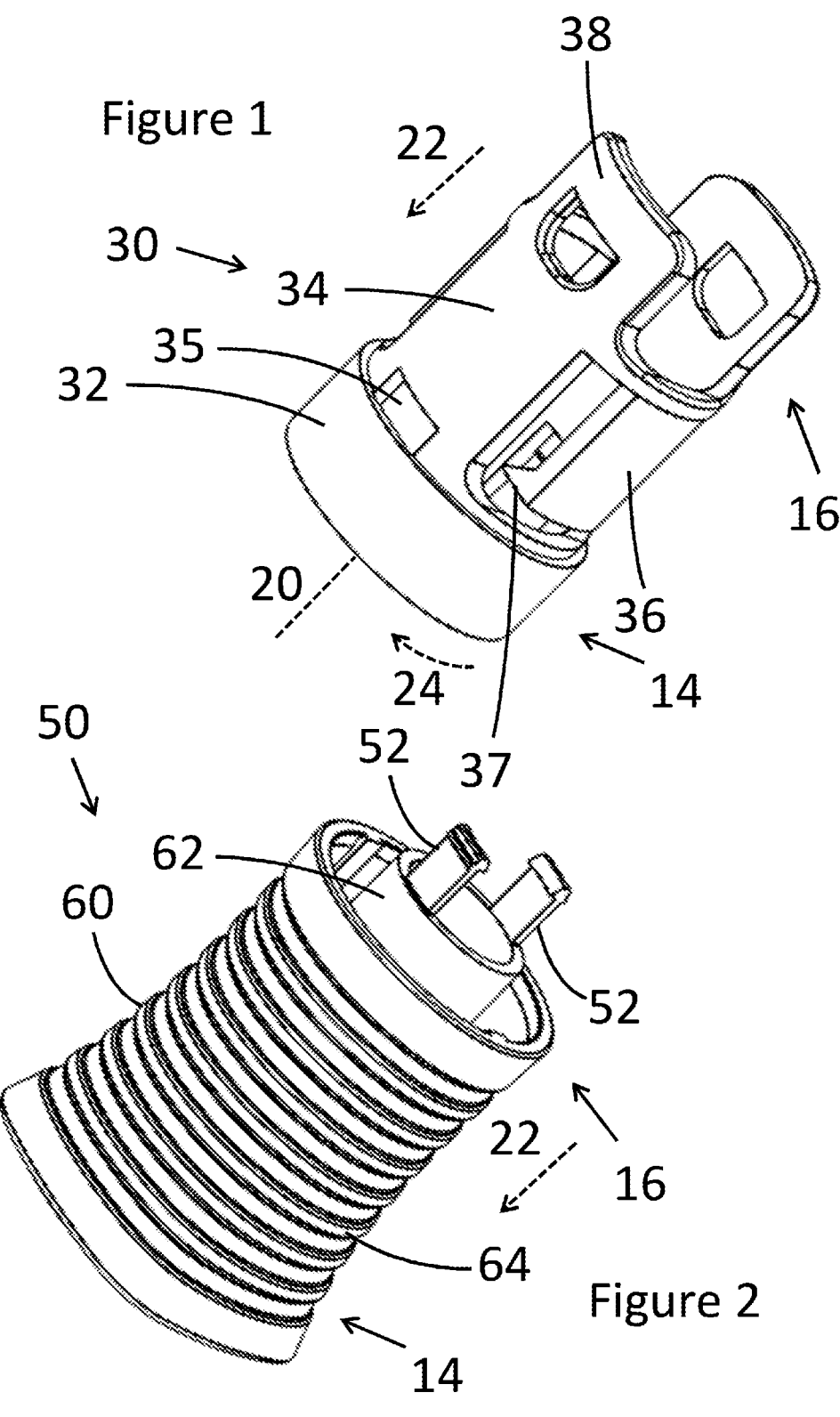
FIG. 1 shows a perspective view of a syringe holder.
FIG. 2 shows a perspective view of a cap.
Figure 3:
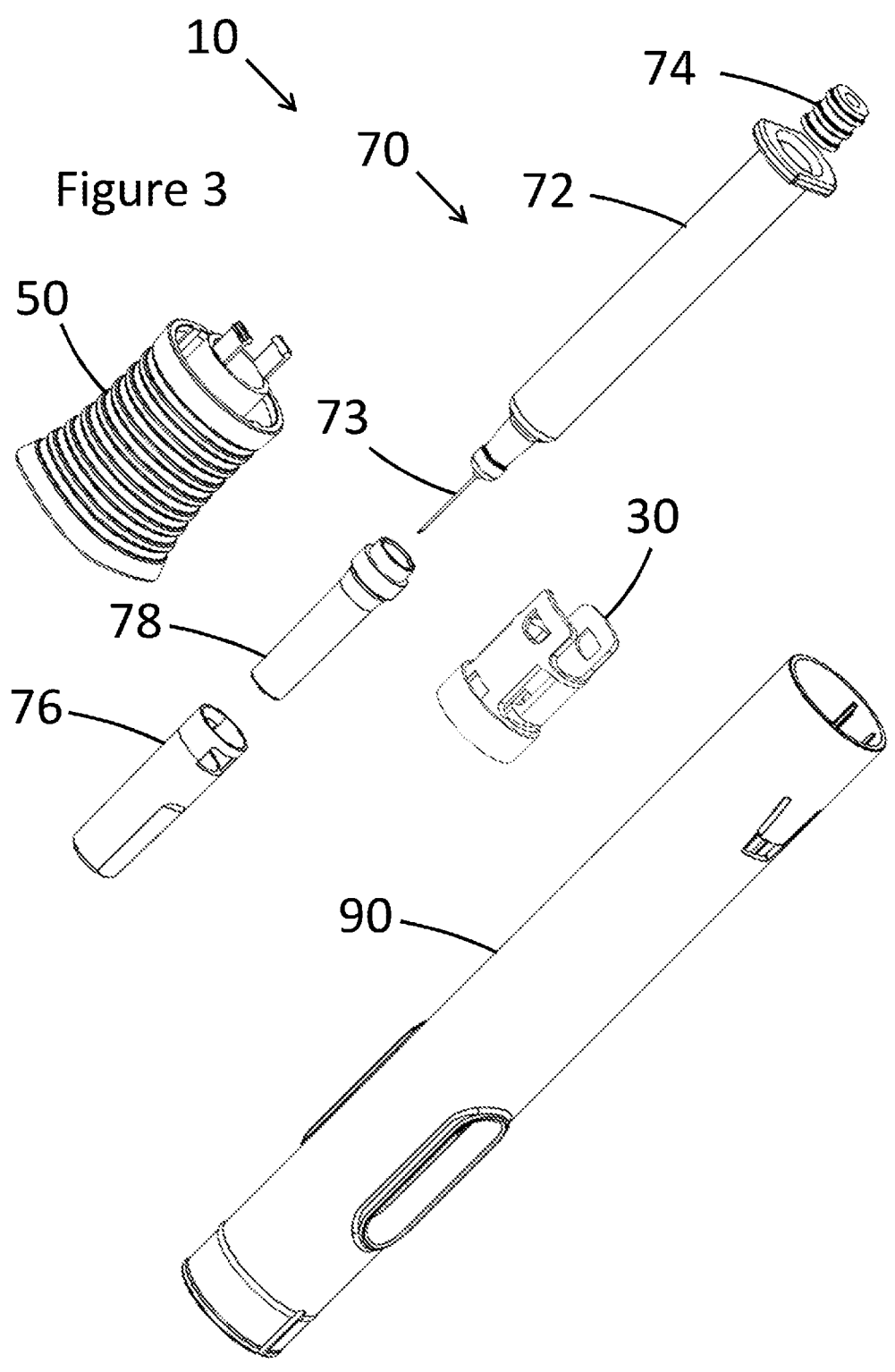
FIG. 3 shows an exploded perspective view of part of an autoinjector including the syringe holder of FIG. 1 and the cap of FIG. 2.

An autoinjector sub-assembly extends along an axis 20 in an axial direction 22 from a proximal end to a distal end. The autoinjector-sub-assembly comprises a cap 50 comprising a tubular housing 60 extending from a proximal closed end to a distal open end and an arm 52 attached to the tubular housing 60, wherein the arm 52 extends in the axial direction 22 from the distal open end.

The autoinjector-sub-assembly comprises a syringe holder 30 comprising a tubular body extending from a proximal end to a distal end and a tubular flange 32 attached to the proximal end of the tubular body, the tubular flange comprising an inner surface 33 facing towards the axis 20. The arm 52 of the cap 50 is between the axis 20 and the inner surface 33 of the flange 32 of the syringe holder 30. The arm 52 of the cap 50 comprises a protrusion 56 extending in the radial direction 26 away from the axis 20. The arm 52 of the cap 50 comprises a protrusion 54 extending in the radial direction 26 towards the axis 20.

FIG. 1 shows a syringe holder 30. The syringe holder 30 extends from a proximal end 14 to a distal end 16 along an axis 20 in an axial direction 22. The syringe holder 30 is tubular, and comprises a flange 32, a body 34, arms 36 and distal protrusions 38. The flange 32, arms 36 and distal protrusions 38 are attached to the body 34. The flange 32 is at the proximal end of the syringe holder 30. The body comprises a cut-out 35 (or alternatively a recess) to accommodate a protrusion 56 of an arm of a cap as outlined below.

Figures 4, 5:
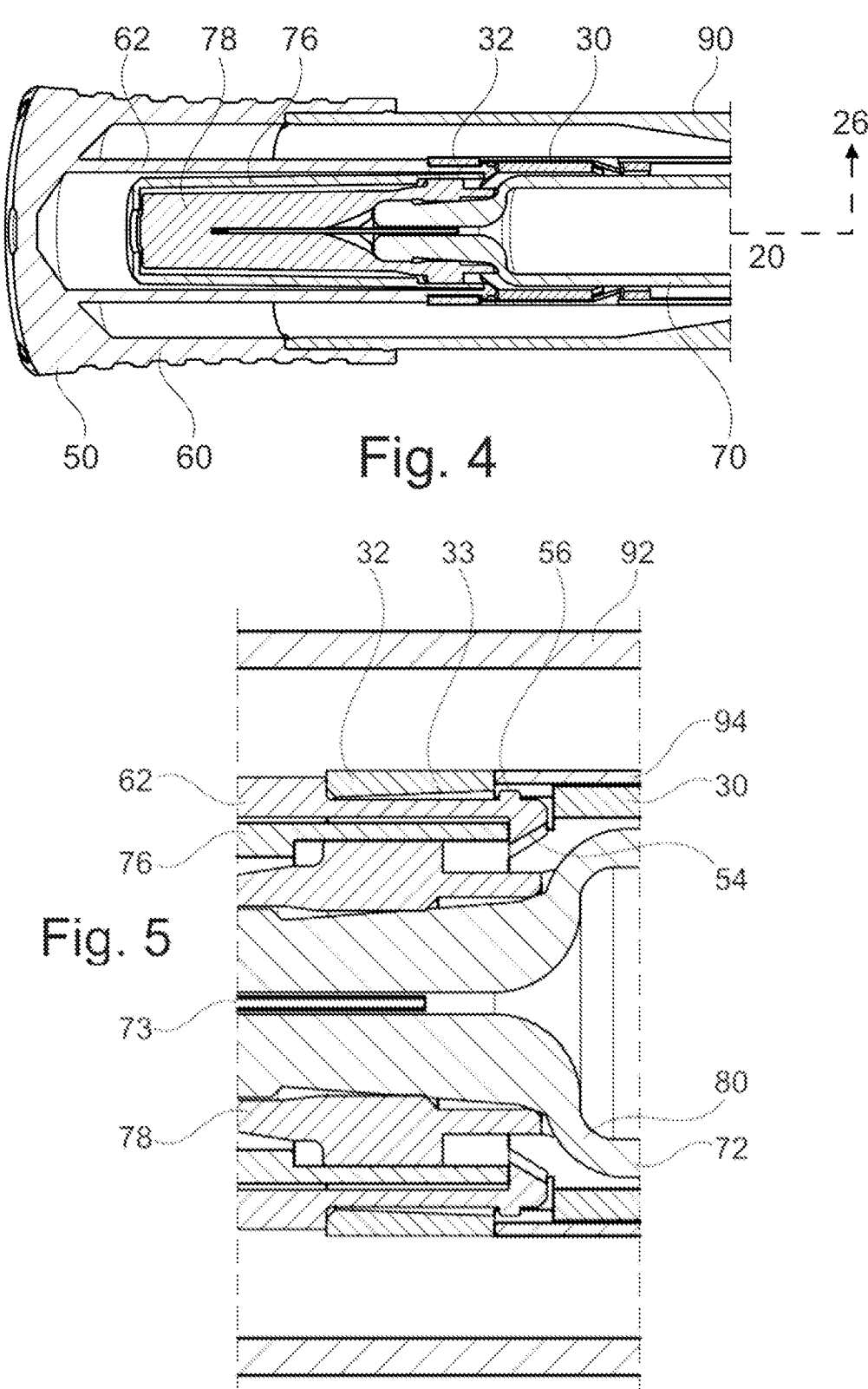
FIG. 4 shows a cross-sectional view of the parts shown in FIG. 3 when assembled.
FIG. 5 shows a close-up of part of FIG. 4.
Figure 6:
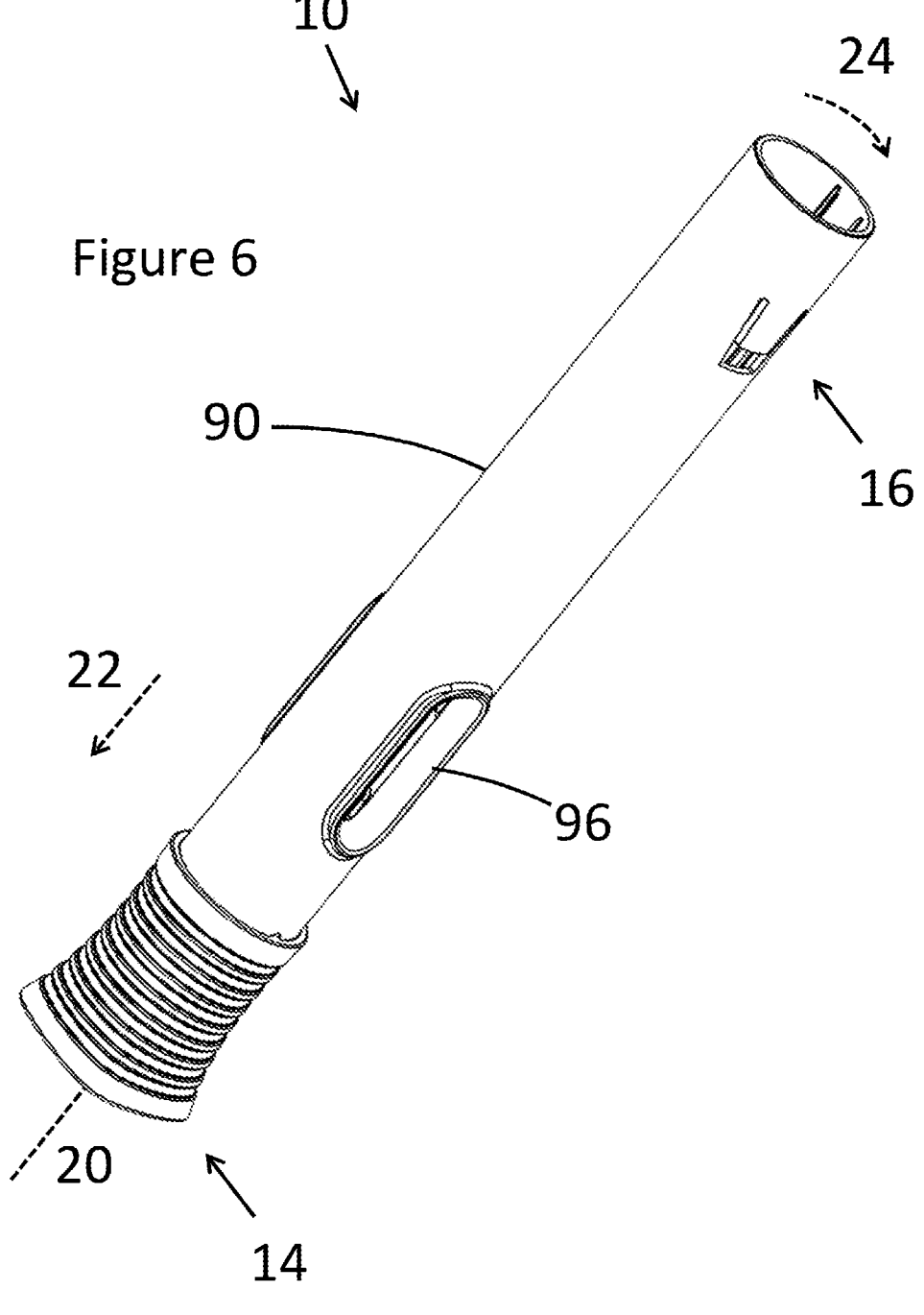
FIG. 6 shows a perspective view of the parts shown in FIG. 3 when assembled.

FIG. 2 shows a cap 50. The cap comprises a tubular housing 62, and extends from a proximal end 14 to a distal end 16. The distal end 16 is open, and the proximal end 14 is closed (see FIG. 4 for example). The cap comprises two arms 52; the arms 52 extend in the axial direction from the distal end of the cap. The arms 52 each comprise a protrusion 54 extending in the radial direction 26 towards the axis and a protrusion 56 extending in the radial direction 26 away from the axis (see also FIG. 5). As can be seen in FIG. 5 in particular, the protrusion 54 extending in the radial direction 26 towards the axis is designed to engage a distally-facing surface of a needle shield of a syringe, and the protrusion 56 extending in the radial direction away from the axis is designed to engage the inner surface of the flange when the cap is removed.

Together, the syringe holder 30 of FIG. 1 and the cap 50 of FIG. 2 make up an autoinjector sub-assembly.

FIGS. 3 to 6 show the syringe holder 30 and cap 50 described above in the context of an autoinjector sub-assembly comprising a syringe 70 and a housing 90. Optionally, the autoinjector sub-assembly could comprise a needle guard configured to shield the needle after the cap has been removed and/or after an injection has been completed. The syringe 70 comprises a medicament container 72, a needle 73 attached to the medicament container 72, a stopper 74, a rigid needle shield 76 and a flexible needle shield 78.

Although not shown in the figures, the autoinjector sub-assemblies described above would typically be combined with a powerpack (rear sub-assembly) to create a complete autoinjector. A typical powerpack would include a rear housing and a power source for injecting the medicament from the syringe. The power source could be mechanical or electrical; one example of a mechanical power source is a spring.

Although this application focusses primarily on autoinjectors, the sub-assemblies described above and the concepts described herein more generally could also be used in other medicament delivery devices more generally, such as in pen injectors.

During assembly, the cap 50 and syringe holder 30 would typically first be attached to the syringe 70, with the cap 50 first being slid on to the syringe from the proximal end of the syringe and the syringe holder 30 subsequently being slid on to the syringe from the distal end of the syringe. The resulting sub-assembly would then be inserted into the housing 90 to create the sub-assembly shown in FIG. 6. A powerpack could then subsequently be inserted into the housing.

During use, the cap is removed by pulling the cap away from the housing (i.e. in the proximal direction). The needle shield of the syringe is pulled away from the syringe by the cap due to the engagement of the protrusion of the arm of the cap extending towards the axis and the distally-facing surface of the needle shield. The flange of the syringe holder can help keep the protrusion of the arm of the cap extending towards the axis and the distally-facing surface of the needle shield engaged as the cap is removed. Once the cap is removed, the steps required for an injection can be carried out. Optionally, the cap can be put back on the device after the injection has been completed.

The particular shape of the syringe holder 30 and the body 40 of the syringe holder are not essential, and other shapes are also possible. In particular, the arms 36 and the distal protrusions 38 are optional. The flange 32 is shown extending entirely around the axis, but may alternatively extend only part of the way around the axis. The flange is shown with an inner surface 33 that is optionally sloped; that is, the flange comprises an inner surface facing towards the axis, and the inner surface is further from the axis at the distal end of the inner surface than at the proximal end of the inner surface. The surface of the inner surface of the flange may be frusto-conical, although other shapes could also be used. Alternatively, the inner surface of the flange could be parallel to the axis.

The arms 36 are optional, and can help support the syringe (specifically, the shoulder 80 of the medicament container is supported by radially inwardly extending protrusions 37 at the proximal end of the arms 36 in the depicted example). In the particular example shown in the figures, the distal end of the arms is attached to the body 40 of the syringe holder, the arms are flexible, and the proximal end of the arms is moveable in the radial direction relative to the body of the syringe holder, which allows radially inwardly extending protrusions 37 of the arms to bend outwards to allow the syringe past (specifically the medicament container of the syringe) during assembly.

The cut-outs 39 in the optional distal protrusion 38 of the syringe holder can engage protrusions on the housing to attach the housing to the syringe holder. The housing could alternatively be attached to a different part of the syringe holder. Alternatively, the syringe holder could be attached to another component such as a part of the powerpack, rather than directly to the housing as in the depicted example. The cut-outs 35 and/or the cut-outs 39 could extend partially or entirely through the body; the cut-outs in the are shown extending entirely through the body in the depicted example.

The cap 50 may be a single integral part or multiple parts. In the example shown in the figures, the cap comprises two tubular housings, namely an outer housing 60 and an inner housing 62 inside the outer housing, and the arms extend from the inner housing (from the distal end of the inner housing in this particular example). Alternatively, the arms could extend from the outer housing. Alternatively, only a single housing could be provided.

In this example, the arms 52 are the distal-most part of the cap, although this is not essential—for example, the outer housing could extend further in the distal direction than the arms. The arms 52 are shown as attached to the inner housing 62, though the arms could alternatively be attached to the outer housing 60.

Optionally, the cap has a grip 64 on the outer surface of the cap, for example on the outer surface of the outer housing as shown in the figures. Optionally, the outer surface of the cap has a wider diameter at the proximal end of the cap than at the distal end of the cap, which can help with gripping and removing the cap. Another optional feature is the gap in the radial direction between the arm 52 of the cap and the inner surface 33 of the flange (see in particular FIG. 5).

The protrusions 54, 56 may vary in shape, depending for example on the shape of the surrounding components with which they interact. In the particular example depicted, the protrusion 54 comprises a proximally-facing surface that abuts a distally-facing surface on the needle shield (in this case the distal end of the needle shield). The proximally-facing surface extends perpendicular to the axis 20, although other angles are also possible. Optionally, as shown in FIG. 5, the protrusion 54 also comprises a distally-facing surface, the surface of which extends at an angle relative to the axis (and not perpendicular to the axis). This can be useful during assembly to help the protrusion 54 pass the needle shield.

The proximally-facing surface of protrusion 54 is shown abutting the needle shield in FIG. 5. Alternatively, the proximally-facing surface of protrusion 54 is spaced apart from distally-facing surface of the needle shield in the axial direction. This gap between the proximally-facing surface of the protrusion 54 and the distally-facing surface of the needle shield means that during removal of the cap, the cap would initially start moving without moving the needle shield. This can make it easier to remove the cap as it reduces the force needed to start moving the cap relative to the rest of the autoinjector.

One example of a syringe 70 is described above, though various shapes and types could be used. Instead of a rigid needle shield and a flexible needle shield, just a single needle shield could be provided (for example a rigid needle shield). Instead of a needle, another medicament delivery member could be provided, such as a jet injector. As such, any mention of a needle herein can be generalised to a medicament delivery member.

The housing 90 is typically tubular. In the example shown, the housing is cylindrical and therefore has a circular cross-section, though other cross-sections such as triangular or square or irregularly-shaped cross-sections are also possible. An optional window 96 is shown in the housing. In the example shown in the figures, the housing comprises an outer tubular portion 92 and an inner tubular portion 94, though other approaches could also be used with the syringe holder and cap described herein.

Some features are shown in the illustrated example with duplicated features, such as various protrusions, arms, cut-outs and windows. This can be useful for various reasons, such as balancing forces and ease of assembly. Having two of each of these features is not essential, however, and in some cases, one, three or more of these features could instead be provided, typically spaced apart around the circumference.

Various modifications to the embodiments described are possible and will occur to those skilled in the art without departing from the present disclosure which is defined by the following claims.

The invention claimed is:

1. An autoinjector sub-assembly extending along a longitudinal axis in an axial direction from a proximal end to a distal end, the autoinjector-sub-assembly comprising
   a cap comprising a tubular housing extending from a proximal closed end to a distal open end and an arm attached to the tubular housing, wherein the arm extends in the axial direction from the distal open end,
   a syringe holder comprising a tubular body extending from a proximal end to a distal end and a tubular flange attached to the proximal end of the tubular body, the tubular flange comprising an inner surface facing towards the longitudinal axis, wherein the tubular body of the syringe holder comprises a cut-out, wherein the cut-out extends entirely through the body of the syringe holder, and wherein the cut-out is aligned in a radial direction relative to the longitudinal axis with the protrusion extending in the radial direction away from the longitudinal axis,
   wherein the arm of the cap is between the longitudinal axis and the inner surface of the flange of the syringe holder,
   wherein the arm of the cap comprises a protrusion extending in the radial direction away from the longitudinal axis, and
   wherein the arm of the cap comprises a protrusion extending in the radial direction towards the longitudinal axis.

2. The autoinjector sub-assembly of claim 1, wherein the inner surface of the flange is further from the longitudinal axis at the distal end of the inner surface than at the proximal end of the inner surface.

3. The autoinjector sub-assembly of claim 1, wherein the flange of the syringe holder extends fully around the longitudinal axis in a circumferential direction relative to the longitudinal axis.

4. The autoinjector sub-assembly of claim 1, wherein the distance of the inner surface from the longitudinal axis continually reduces when travelling along the flange from the distal end of the inner surface to the proximal end of the inner surface.

5. The autoinjector sub-assembly of claim 1, wherein the syringe holder comprises a flexible arm extending in the axial direction from a proximal end to a distal end, wherein the distal end of the arm is attached to the body and the proximal end of the arm is movable in the radial direction relative to the body.

6. The autoinjector sub-assembly of claim 1, wherein the cap is a single integral part.

7. The autoinjector sub-assembly of claim 1, further comprising a syringe, the syringe comprising a medicament container, a medicament delivery member shield, and a medicament delivery member attached to the medicament container, wherein the medicament delivery member is inside the medicament delivery member shield.

8. The autoinjector sub-assembly of claim 7, wherein a proximally-facing surface of the protrusion extending in the radial direction towards the longitudinal axis abuts a distally facing surface of the medicament delivery member shield.

9. The autoinjector sub-assembly of claim 7, wherein a proximally-facing surface of the protrusion extending in the radial direction towards the longitudinal axis is spaced apart in the axial direction from a distally facing surface of the medicament delivery member shield.

10. The autoinjector sub-assembly of claim 1, comprising a housing, wherein the syringe holder is attached to the housing.

11. The autoinjector sub-assembly of claim 1, wherein the protrusion extending in the radial direction away from the longitudinal axis is configured to engage the inner surface of the flange when the cap is removed from an autoinjector comprising the autoinjector sub-assembly.

12. The autoinjector sub-assembly of claim 1, wherein the protrusion extending in the radial direction towards the longitudinal axis is configured to engage a distally-facing surface of a medicament delivery member shield of a syringe when the cap is removed from an autoinjector comprising the autoinjector sub-assembly.

13. The autoinjector sub-assembly of claim 1, wherein the tubular body of the syringe holder comprises a recess, and wherein the recess is aligned in a radial direction relative to the longitudinal axis with the protrusion extending in the radial direction away from the longitudinal axis.

14. An autoinjector comprising
   a housing; and
   the autoinjector sub-assembly of claim 1.

* * * * *